(12) United States Patent
Bachmann et al.

(10) Patent No.: US 11,124,532 B2
(45) Date of Patent: Sep. 21, 2021

(54) CHIRAL METAL COMPLEX COMPOUNDS

(71) Applicant: Hoffmann-La Roche Inc., Little Falls, NJ (US)

(72) Inventors: Stephan Bachmann, Basel (CH); Matthias Beller, Rostock (DE); Marcel Garbe, Rostock (DE); Kathrin Junge, Rostock (DE); Michelangelo Scalone, Basel (CH)

(73) Assignee: Hoffmann-La Roche Inc., Little Falls, NY (US)

( * ) Notice: Subject to any disclaimer, the term of this patent is extended or adjusted under 35 U.S.C. 154(b) by 0 days.

(21) Appl. No.: 16/599,003

(22) Filed: Oct. 10, 2019

(65) Prior Publication Data

US 2020/0040021 A1    Feb. 6, 2020

Related U.S. Application Data

(63) Continuation of application No. PCT/EP2018/058949, filed on Apr. 9, 2018.

(30) Foreign Application Priority Data

Apr. 11, 2017 (EP) .................... 17165855

(51) Int. Cl.
*C07F 15/02* (2006.01)
*C07F 13/00* (2006.01)

(52) U.S. Cl.
CPC ............. *C07F 15/02* (2013.01); *C07F 13/00* (2013.01)

(58) Field of Classification Search
None
See application file for complete search history.

(56) References Cited

U.S. PATENT DOCUMENTS 7,291,753 B2 * 11/2007 Abdur-Rashid ....... B01J 31/189
546/329

FOREIGN PATENT DOCUMENTS

EP    17165855.2    4/2017
WO    2004/096735 A2    11/2004

OTHER PUBLICATIONS

Garbe et al. Angew. Chem. Int. Ed. 2017, 56, 11237-11241.*
Anderson et al., "Evolution and Prospects of the Asymmetric Hydrogenation of Unfunctionalized Olefins" J. Am. Chem. Soc 139:1346-1356 ( 2017).
Burk et al., "New Chiral Phospholanes; Synthesis, Characterization, and Use in Asymetric Hydrogenation Reactions" Tetrahedron Asymmetry 2(7):569-592 ( 1991).
CAS Registry No. 791630-00-7 ( Dec. 2, 2004).
Danopoulos et al., "The synthesis of tridentate dialkylamino ligands containing tertiary phosphorus or arsenic donors" Polyhedron 9(19):2413-2418 ( 1990).
Hammerer et al., "Synthesis of Josiphos-Type Bisphospholane Ligands" Synthesis 44:2793-2797 ( 2012).
International Preliminary Report on Patentability (IPRP) for PCT/EP2018/058949 dated Oct. 15, 2019.
International Search Report for PCT/EP2018/058949 dated Jul. 2, 2018.
Morris et al., "Ketone Asymmetric Hydrogenation Catalyzed by P-NH-P' Pincer Iron Catalysts: An Experimental and Computational Study" ACS Catal. 7:316-326 ( 2017).
Sheldrick et al., "A short history of SHELX" Acta Cryst. A64:112-122 ( 2008).
Sheldrick et al., "Crystal structure refinement with SHELXL" Acta Cryst. C71:3-8 ( 2015).

* cited by examiner

*Primary Examiner* — Clinton A Brooks
(74) *Attorney, Agent, or Firm* — Bradley E. Davis

(57) ABSTRACT

The invention comprises novel chiral metal complex compounds of the formula

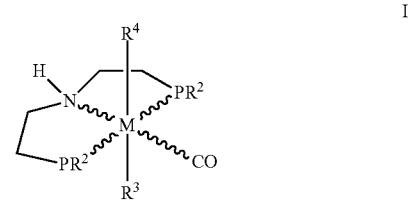

wherein M, $PR^2$, $R^3$ and $R^4$ are outlined in the description, its stereoisomers, in the form as a neutral complex or a complex cation with a suitable counter ion. The chiral metal complex compounds can be used in asymmetric reactions, particularly in asymmetric reductions of ketones, imines or oximes.

25 Claims, No Drawings

CHIRAL METAL COMPLEX COMPOUNDS

CROSS-REFERENCE TO RELATED APPLICATIONS

This application is a continuation of International Application No. PCT/EP2018/058949, filed Apr. 9, 2018, which claims benefit of priority to EP Application No. 17165855.2 filed Apr. 11, 2017, each of which are incorporated herein by reference in its entirety.

The invention relates to novel chiral metal complex compounds of the formula

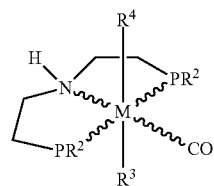

I wherein M, $PR^2$, $R^3$ and $R^4$ are as defined below and its stereoisomers in the form as a neutral complex or a complex cation with a suitable counter ion.

The invention also relates to processes for the preparation of the chiral metal complexes and to their use in asymmetric reactions, particularly in asymmetric reductions of C=X double bonds, namely of ketones (C=O), α- or β-ketoesters (α: —(C=O)—(C=O)—OR) or β: —(C=O)—CR$_2$—(C=O)—OR), imines (—C=N—R) or oximes (—C=N—OH).

Research in the field of catalysts for asymmetric reaction such as in asymmetric hydrogenations tend to move away from the platinum group metal catalysts to environmentally friendly non platinum group metal catalysts. (P. G. Anderson et al., J. Am. Chem. Soc. 2017, 139, 1346; R. H. Morris et al., ACS Catal. 2017, 7, 316).

Object of the present invention is to provide chiral metal complex catalysts which are both environmentally friendly and which show high enantioselectivity and conversion rates.

The object could be reached with the novel chiral metal complex compounds of the formula

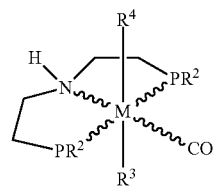

I wherein ⁓ denotes either a broken bond (a) or a wedged bond (b)

a) ⋯ b) ▬

M is a metal selected from the manganese group or the iron group of the periodic system;

$PR^2$ is

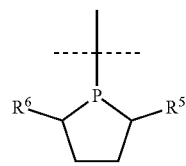

IIa wherein $R^5$ and $R^6$ independent of each other are $C_{1-4}$-alkyl or aryl; or

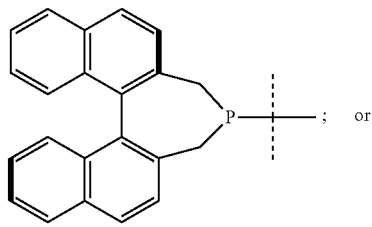

IIb or

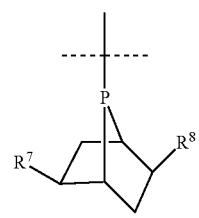

IIc wherein $R^7$ and $R^8$ independent of each other are $C_{1-4}$-alkyl;

$R^3$ is CO, halogen or hydrogen and
$R^4$ is CO, halogen or H—BH$_3$;
and its stereoisomers in the form as a neutral complex or a complex cation with a suitable counter ion.

Unless otherwise defined, all technical and scientific terms used herein have the same meaning as commonly understood by one of ordinary skill in the art to which this invention belongs. Although methods and materials similar or equivalent to those described herein can be used in the practice or testing of the invention, suitable methods and materials are described below.

The term "chiral" denotes the ability of non-superimposability with the mirror image, while the term "achiral" refers to embodiments which are superimposable with their mirror image. Chiral molecules are optically active, i.e., they have the ability to rotate the plane of plane-polarized light. Whenever a chiral center is present in a chemical structure, it is intended that all stereoisomers associated with that chiral center are encompassed by the present invention.

The term "chiral" signifies that the molecule can exist in the form of optically pure enantiomers, mixtures of enantiomers, optically pure diastereoisomers or mixtures of diastereoisomers.

In a preferred embodiment of the invention the term "chiral" denotes optically pure enantiomers or optically pure diastereoisomers.

The term "stereoisomer" denotes a compound that possesses identical molecular connectivity and bond multiplicity, but which differs in the arrangement of its atoms in space.

The term "diastereomer" denotes a stereoisomer with two or more centers of chirality and whose molecules are not mirror images of one another. Diastereomers have different physical properties, e.g. melting points, boiling points, spectral properties, and reactivities.

The term "enantiomers" denotes two stereoisomers of a compound which are non-superimposable mirror images of one another.

In the structural formula presented herein a broken bond (a) denotes that the substituent is below the plane of the paper and a wedged bond (b) denotes that the substituent is above the plane of the paper.

a) ⋯⋯⋯ b) ▬▬◼

The spiral bond (c) denotes both options i.e. either a broken bond (a) or a wedged bond (b).

c) ⌇⌇⌇

The term "$C_{1-4}$-alkyl" denotes a monovalent linear or branched saturated hydrocarbon group of 1 to 4 carbon atoms. Examples of $C_{1-4}$-alkyl include methyl, ethyl, propyl, isopropyl, n-butyl, iso-butyl, sec-butyl, or tert-butyl.

The term "halogen" denotes fluoro, chloro, bromo, or iodo.

The term "pseudohalogen" denotes analogues of halogens whose chemistry resembles that of halogens. Examples of pseudohalogens are cyano, isocyanide, cyanate or isocyanate.

The term "aryl" denotes a monovalent aromatic carbocyclic mono- or bicyclic ring system comprising 6 to 10 carbon ring atoms which optionally may be substituted. Examples of aryl moieties include phenyl and naphthyl. Phenyl is the preferred aryl group.

The term "optionally substituted" in connection with the term "aryl" denotes that the aryl group may be unsubstituted or substituted by one or more substituents, independently selected from $C_{1-4}$-alkyl, $C_{1-4}$-alkoxy or halogen.

M stands for a metal of the manganese group or the iron group of the periodic system.

Suitable metals of the manganese group are manganese or rhenium, preferably manganese.

Suitable metals of the iron group are iron, ruthenium or osmium, preferably iron.

In a preferred embodiment of the present invention the metal M is selected from the manganese group or the iron group of the periodic system more preferably the metal M is selected from manganese or iron.

$PR^2$ stands for the ligands

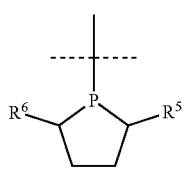

IIa wherein $R^5$ and $R^6$ independent of each other are $C_{1-4}$-alkyl or aryl, preferably $C_{1-4}$-alkyl or phenyl, more preferably $C_{1-4}$-alkyl and even more preferably methyl; or

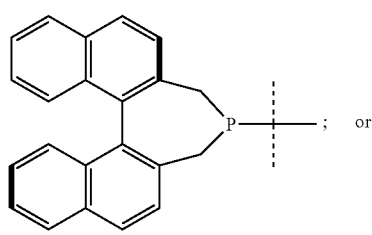

IIb

; or

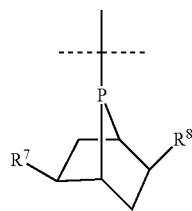

IIc wherein $R^7$ and $R^8$ independent of each other are $C_{1-4}$-alkyl, more preferably methyl.

$PR^2$ particularly is the ligand of formula IIa1

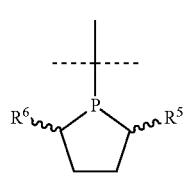

IIa1 wherein ⌇⌇⌇, $R^5$ and $R^6$ are as above, but wherein $R^5$ and $R^6$ preferably are $C_{1-4}$-alkyl, more preferably methyl.

More particularly $PR^2$ is the ligand of formula IIa2' or IIa2"

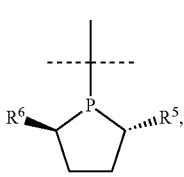

IIa2'

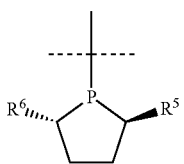

IIa2"

wherein $R^5$ and $R^6$ are as above, but preferably is $C_{1-4}$-alkyl, more preferably methyl.

In a preferred embodiment of the present invention the chiral metal complex compounds have the formula Ia

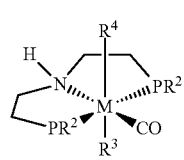

Ia wherein M, $PR^2$, $R^3$ and $R^4$ are as above in the form as a neutral complex or a complex cation with a suitable counter ion.

Applying manganese as preferred metal M the chiral manganese complex compounds have the formula Ib

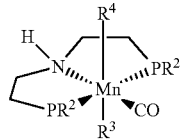

wherein PR², R³ and R⁴ are as above in the form as a neutral complex or a complex cation with a suitable counter ion, more preferably the chiral manganese complex compounds have the formula Id

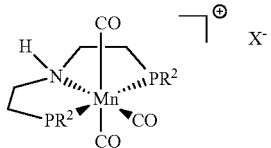

wherein PR² is as above and X is a halogen or a pseudo-halogen.

X preferably stands for a halogen, more preferably for bromine or chlorine, even more preferably for bromine.

Likewise with iron as preferred metal M the chiral iron complex compounds have the formula Ic

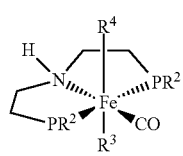

wherein PR², R³ and R⁴ are as above, more preferably the chiral iron complex compounds have the formula Ie

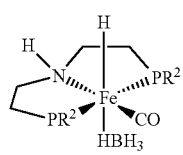

wherein PR² is as above.

Most preferred chiral metal complexes have the formula If

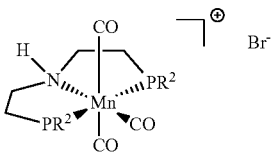

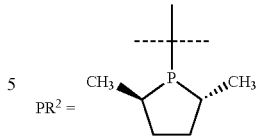

or the formula Ig

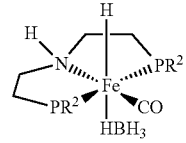

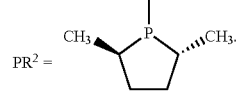

The invention also comprises a process for the preparation of the chiral metal complex compound of formula I which comprises the reaction of a Bis(phospholanoethyl)amine derivative of the formula III

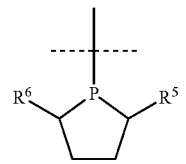

wherein PR² is as above with a metal salt. The metal salt suitable for the reaction largely depends on the metal M applied.

The bis(phospholanoethyl)amine derivative of the formula III can be synthesized starting from the respective phosphines HPR² following methods known in the art.

Accordingly for the phosphine wherein PR² stands for the ligand

IIa the synthesis of the Bis(phospholanoethyl)amine derivative of the formula III with $R^5$ and $R^6$ being methyl can be accomplished according to M. J. Burk, J. E. Feaster, R. L. Harlow, *Tetrahedron: Asymmetry* 1991, 2, 569-592 via the reaction of dimethylphospholane with bis(2-chloroethyl)trimethylsilylamine.

The Bis(phospholanoethyl)amine derivative of the formula III with the phosphine ligand PR² of the formula

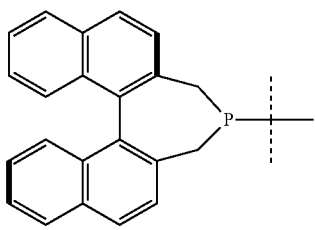

is commercially available (CAS No. 791630-00-7) for instance from Sigma-Aldrich.

For the phosphine with the ligand $PR^2$

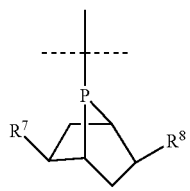

with $R^7$ and $R^8$ as described above can be accomplished in analogy of the ligand $PR^2$ of formula IIa according to M. J. Burk, J. E. Feaster, R. L. Harlow, *Tetrahedron: Asymmetry* 1991, 2, 569-592 via the reaction of the phosphine with the ligand of formula IIc with bis(2-chloroethyl) trimethylsilylamine.

The synthesis of the bis(phospholanoethyl)amine derivative of the formula III can be accomplished according to M. J. Burk, J. E. Feaster, R. L. Harlow, *Tetrahedron: Asymmetry* 1991, 2, 569-592.

The preparation of the chiral metal complex compounds of formula Id

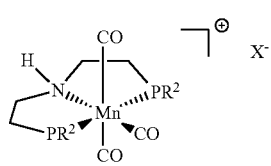

wherein $PR^2$ is as above comprises the reaction of a bis(phospholanoethyl)amine derivative of the formula III

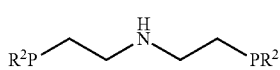

wherein $PR^2$ is as above with $Mn(CO)_5X$, wherein $X^-$ is a halogen or a pseudohalogen, preferably a halogen, more preferably chlorine or bromine and even more preferably bromine.

The reaction is expediently performed in a suitable organic solvent under inert gas atmosphere at reaction temperatures from 20° C. to 150° C., preferably from 80° C. to 110° C.

Suitable solvents are non-polar solvents such as aromatic hydrocarbons like toluene or benzene.

The complexes can be isolated by standard techniques and further be purified via crystallization.

The preparation of the chiral metal complex compound of formula Ie

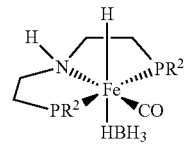

comprises the reaction of a Bis(phospholanoethyl)amine derivative of the formula III

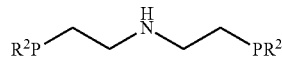

wherein $PR^2$ is as above with $FeX_2$, wherein X is a halogen and with carbon monoxide to form an iron complex intermediate of formula IV

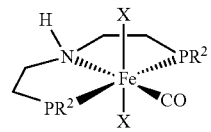

and the subsequent transformation into the chiral metal complex compound of formula Ie with a suitable hydride forming agent.

$FeX_2$ preferably is iron chloride or iron bromide, more preferably iron bromide.

The reaction of a Bis(phospholanoethyl)amine derivative of the formula III with $FeX_2$ usually takes place in a suitable organic solvent such as in polar aprotic solvents like tetrahydrofuran at reaction temperatures from 0° C. to 50° C., preferably from 20° C. to 30° C. during 2 h to 8 h.

The subsequent reaction with carbon monoxide to form the intermediate of formula IV can take place at reaction temperatures from 0° C. to 50° C., preferably from 20° C. to 30° C. during 0.5 h to 6 h.

Isolation of the intermediate can easily be accomplished by removing the solvent and washing of the crude intermediate compound with a suitable solvent e.g. with ethanol.

The chiral iron complex intermediate of formula IV

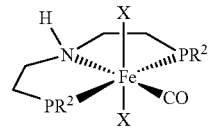

wherein $PR^2$ is as above and X is a halogen are compounds which are not known in the state of the art and therefore are also an embodiment of the present invention.

In a more preferred embodiment X is chlorine or bromine, more preferably bromine.

PR² particularly is the ligand of formula IIa1

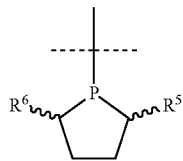

IIa1 wherein ⁓⁓⁓ , R⁵ and R⁶ are as above, but wherein R⁵ and R⁶ preferably are $C_{1-4}$-alkyl, more preferably methyl.

More particularly PR² is the ligand of formula IIa2' or IIa2''

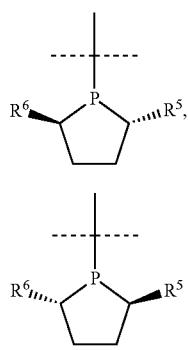

IIa2'

IIa2'' wherein R⁵ and R⁶ are as above, but preferably is $C_{1-4}$-alkyl, more preferably methyl.

Most preferred chiral iron complex intermediate has the formula IV wherein X is bromine and PR² has the formula IIa2' with R⁵ and R⁶ methyl.

Suitable hydride forming agent for the transformation of the chiral iron complex intermediate of formula IV into the chiral metal complex compound of formula Ie can be selected from complex metal hydrides like lithium aluminum hydride, diisobutyl aluminum hydride or sodium borohydride, preferably sodium borohydride.

The reaction usually takes place in a suitable organic solvent such as in non-polar solvents like toluene at reaction temperatures of 0° C. to 50° C.

Isolation of the desired iron complex can happen via removal of the solvent and washing of the crude complex compound with a suitable solvent e.g. with n-heptane.

In a further embodiment of the present invention the chiral metal complex compounds described above can be used in the catalysis of asymmetric reactions, particularly asymmetric reduction, more particularly asymmetric reductions of C=X double bonds, namely of ketones (C=O), α- or β-ketoesters (α: —(C=O)—(C=O)—OR) or β: —(C=O)—CR₂—(C=O)—OR), imines (—C=N—R) or oximes (—C=N—OH).

In a more preferred embodiment of the present invention the chiral metal complex compounds described above can be used in the catalysis of asymmetric hydrogenations of C=X double bonds, namely of ketones, ketoesters, imines or oximes, particularly of ketones.

The chiral metal complexes are active on a broad substrate spectrum of compounds with C=X functionality.

Thus for the ketones dialkylketones, arylalkylketones, cycloalkylalkyl ketones, α- and β-ketoesters, cycloalkanones, heterocyclylalkylketones or even ketogroup containing heterocyclic compounds are suitable substrates.

The reaction conditions for the asymmetric hydrogenation largely depends on the selected chiral metal complex and the substrate, but in principle the reaction conditions are known to the skilled in the art.

In a typical procedure for the asymmetric hydrogenation of ketones with the preferred manganese complex of formula Id the complex is dissolved under inert gas atmosphere in a suitable organic solvent in the presence of a base. Thereafter the ketone substrate is added and the hydrogenation is performed in an autoclave as a rule at elevated temperature and a hydrogen pressure of 5 bar to 100 bar, preferably between 10 bar and 60 bar.

In a typical procedure for the asymmetric hydrogenation of ketones with the preferred iron complex of formula Ie the complex is dissolved under inert gas atmosphere in a suitable organic solvent. Thereafter the ketone substrate is added and the hydrogenation is performed in an autoclave as a rule at elevated temperature and a hydrogen pressure of 5 bar to 100 bar, preferably between 10 bar and 60 bar. The following examples shall further illustrate the invention.

EXAMPLES

Abbreviations

MeOH methanol
DMSO dimethyl sulfoxide
EA element analysis
RT room temperature
TBAF Tetra-n-butylammonium fluoride
THF tetrahydrofuran
X-Ray Crystal Structure Analysis of X:

Data were collected on a Bruker Kappa APEX II Duo diffractometer. The structures were solved by direct methods (SHELXS-97: Sheldrick, G. M. Acta Cryst. 2008, A64, 112.) and refined by full-matrix least-squares procedures on F2 (SHELXL-2014: G. M. Sheldrick, Acta Cryst. 2015, C71, 3.). XP (Bruker AXS) was used for graphical representations.

1. Ligand Synthesis 1.1 Synthesis of (2R,5R)-2,5-dimethylphospholane

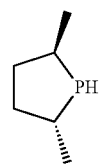

The title compound was synthesized according to the reported procedure (T. Hammerer, A. Dambkes, W. Braun, A. Salzer, G. Franció, W. Leitner, *Synthesis* 2012, 44, 2793-2797).

To a cooled solution of (R,R)-2,5-dimethyl-1-(trimethylsilyl) phospholane (9.42 g, 50.0 mol) with an isopropanol cooling bath (−79° C.) MeOH (1.63 g, 51.0 mol) was added dropwise. The resulting solution was allowed to warm up to room temperature and stirred overnight. The side products were condensed into another Schlenk flask by heating the solution up to 60° C. The product was isolated as a colorless liquid with a yield of 95% (5.52 g, 47.5 mmol).

1.2 Syntheses of Bis(2-chloroethyl)trimethylsilylamine

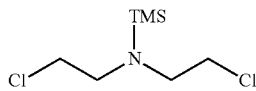

The title compound was synthesized following the reported procedure (A. A. Danopoulos, A. R. Willis, P. G. Edwards, *Polyhedron* 1990, 9, 2413-2418).

To a stirred and cooled (0° C.) suspension of Bis(2-chloroethyl)amine hydrochloride (10 g, 56.0 mmol) in 100 mL Et$_2$O, 0.25 mL DMSO and Triethylamine (17.0 g, 168.0 mmol) Trimethylchlorosilane (21.3 g, 196 mmol) was added dropwise over half an hour at 0°. The solution was stirred for one hour at 0° C., warmed up to room temperature and stirred for further 3-5 days. The solution was filtered and the volatiles of the liquid portion were removed in vacuo and the product was achieved as yellow viscose liquid (9.96 g, 46.5 mmol, 83% yield).

1.3 Synthesis of Bis(2-((2R,5R)-2,5-dimethylphospholanoethyl))amine

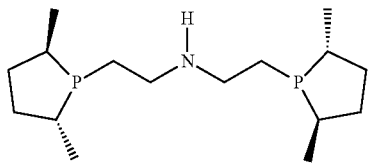 [SMILES: C[C@@H]1CC[C@@H](C)P1CCNCCP1[C@H](C)CC[C@H]1C]

The title compound was synthesized referring to the reported procedure (M. J. Burk, J. E. Feaster, R. L. Harlow, *Tetrahedron. Asymmetry* 1991, 2, 569-592).

(2R,5R)-2,5-dimethylphospholane (6.9 g, 0.059 mmol) was dissolved in 80 mL n-hexane and cooled to −79° C. n-Butyllithium (2.5 M in n-hexane, 25 mL, 62.5 mmol) was added dropwise to the solution. The solution was stirred for half an hour at this temperature, warmed up to room temperature and the resulting slightly yellow solution was stirred for further five hours. 10 mL of THF was added and the solution was again cooled down to −79° C. 6.32 g (29.5 mmol) Bis(2-chloroethyl)trimethylsilylamine diluted in 10 mL of THF was dropwise added while a white solid precipitated. The slightly yellow suspension was stirred for 16 h at room temperature. Afterwards 30 mL of water and 60 mL of TBAF (1M solution in THF, 60 mmol) was added and the resulting two-phase system was stirred for further 3-5 days. Most of the organic solvents were removed in vacuo and the product was extracted three times with Et$_2$O from the aqueous phase. The organic layer was dried over MgSO$_4$, filtered, the volatiles of the liquid portion were removed in vacuo and the yellow product was dried in vacuo (6.76 g, 22.4 mmol, 71% yield). The pincer ligand was used without further purification.

$^1$H NMR (400.13 MHz; CD$_3$Cl): δ=1.08-1.12 (dd, 6H, CH$_3$, J=7.2 Hz); 1.16-1.23 (dd, 6H, CH$_3$, J=7.2 Hz; m, 2H, CH$_2$); 1.34-1.47 (m, 4H, CH$_2$); 1.61-1.68 (m, 2H, CH$_2$); 1.84-1.92 (m, 2H, CHI); 1.93-2.02 (m, 2H, CH$_2$); 2.03-2.15 (m, 4H, CH$_2$, CHI); 2.62-2.78 (m, 4H, CH$_2$), 3.8 (br, 1H, NH).

$^{31}$P NMR (121.5 MHz; CD$_3$Cl): δ=−5.2 ppm.

2. Complex Synthesis

2.1 Synthesis of Manganese Complexes

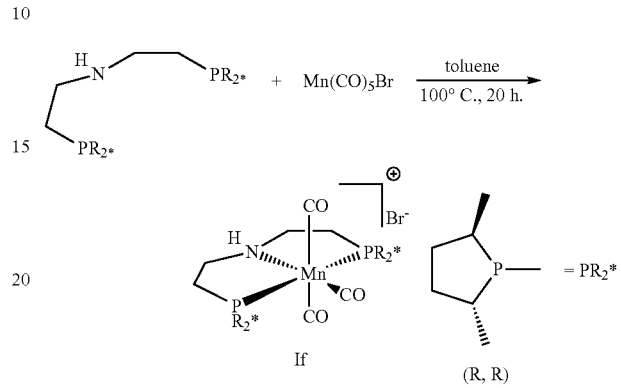

To the suspension of [MnBr(CO)$_5$] (275 mg, 1 mmol) in toluene (20 mL) Bis(2-((2R,5R)-2,5-dimethylphospholanoethyl))amine (331.5 mg, 1.1 mmol, dissolved in 2 mL toluene) was added. The [MnBr(CO)$_5$] was dissolved, the solution was heated up to 100° C. and further stirred for 20 h under argon flow. The reaction mixture was cooled to room temperature and concentrated in vacuo resulting in a yellow solid with red inclusions. The crude solid was washed three times with 5 mL of pentane resulting in a clean yellow/orange solid (359.5 mg, 72.4 mmol, 72% yield).

$^{31}$P{$^1$H} NMR (122 MHz, C$_6$D$_6$): δ=97.14.

IR-ATR (solid) $\bar{υ}$ [cm$^{-1}$]: 2009 (s, $\bar{υ}$ CO), 1908 (s, $\bar{υ}$ CO), 1821 (s, $\bar{υ}$ CO).

EA % ber. (gef) C$_{17}$H$_{38}$BrMnNO$_3$P$_2$, M=520.27 g/mol: C, 43.86 (44.97); H, 6.39 (6.61) N, 2.69 (2.74).

2.2 Synthesis of Iron Complexes a) Synthesis of the Precursor

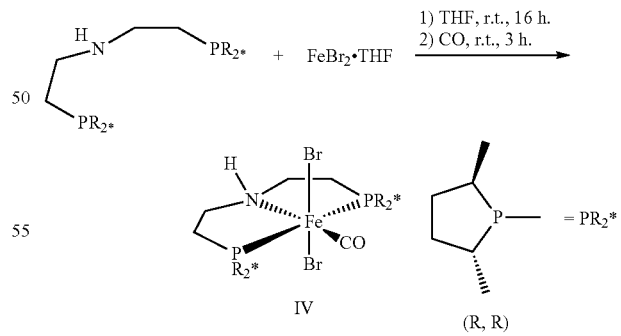

2.07 g of Bis(2-((2R,5R)-2,5-dimethylphospholanoethyl))amine (6.8 mmol) was dissolved in 30 mL THF. Afterwards a solution of FeBr$_2$·THF (2.84 g, 6.8 mmol) in 20 mL THF was added. The resulting brown/yellow solution was stirred overnight at room temperature. By reacting with CO over three hours a blue solid was formed. The solvent was removed in vacuo and the resulted crude solid was washed with 5 mL EtOH getting a pure compound with a yield of 63% (2.35 g, 4.3 mmol).

$^{1}$H NMR (400.13 MHz; CD$_3$Cl): δ=1.11-1.16 (m, 6H, CH$_3$); 1.22-1.38 (m, 3H, P—CH$_2$); 1.42-1.52 (m, 2H, P—CH$_2$); 1.59-1.78 (m, 9H, 2×CH$_3$; P—CH$_2$); 1.80-1.90 (m, 1H, P—CH$_2$); 1.99-2.16 (m, 3H, P—CH); 2.29-2.36 (m, 1H, P—CH); 2.37-2.45 (m, 1H, P—CH); 2.54-2.78 (dd, 2H, N—CH$_2$), 2.82-2.92 (m, 1H, N—CH$_2$); 2.94-3.04 (m, 2H, P—CH); 3.14-3.26 (m, 1H, N—CH$_2$); 4.32-4.44 (br, 1H, NH).

$^{31}$P{$^{1}$H} NMR (122 MHz, C$_6$D$_6$): δ=95.91 (d, J$_{PP}$=174.19 Hz), 98.54 (d, J$_{PP}$=174.19).

IR-ATR (solid) $\bar{υ}$ [cm$^{-1}$]: 1935 (s, $\bar{υ}$ CO).

b) Synthesis of Iron Complex Ie 690 mg of IV (1.27 mmol) was dissolved in 20 mL of benzene or toluene. A freshly prepared solution of NaBH$_4$ (383 mg, 10.12 mmol, in 20 mL EtOH) was added dropwise to the solution whereas a gas evolution was directly noticeable. After stirring the solution for 3-5 h the solvents were removed and the remaining solid was dried in vacuo. The product was extracted with benzene or toluene (in total 40 mL) and the solvent was afterwards removed in vacuo. The crude solid was washed three times with 10 mL of n-heptane and the expected product was achieved with a yield of 80% (403 mg).

$^{1}$H-NMR (300 K, C$_6$D$_6$, 400.13 MHz): δ=−19.20 (t, 1H, Fe—H, $^{2}$J$_{HP}$=51.85 Hz, (minor isomer)), −18.80 (t, 1H, Fe—H, $^{2}$J$_{HP}$=51.75 Hz, (major isomer)), −2.77 (bs, 4H, HBH$_3$), 0.95 (m, 3H, CH$_3$), 1.15 (m, 3H, CH—CH$_2$), 1.25 (m, 5H, CH$_3$ and P—CH$_2$ and CH—CH$_2$), 1.32 (m, 1H, CH—CH$_2$), 1.41 (m, 3H, CH$_3$), 1.51 (m, 2H, N—CH$_2$), 1.58 (m, 1H, CH), 1.66 (m, 1H, P—CH$_2$), 1.73 (m, 6H, CH$_3$, P—CH$_2$ and CH—CH$_2$), 1.91 (m, 4H, CH—CH$_2$ and CH), 2.08 (m, 1H, P—CH$_2$), 2.27 (m, 1H, CH), 2.62 (m, 3H, CH and N—CH$_2$), 3.76 (m, 1H, N—H).

$^{31}$P-NMR—major isomer (300 K, C$_6$D$_6$, 100.616 MHz): δ=109.18 (d, 1P, $^{2}$J$_{PP}$=122.93 Hz), 107.02 (d, 1P, $^{2}$J$_{PP}$=120.75 Hz).

$^{31}$P-NMR—minor isomer (300 K, C$_6$D$_6$, 100.616 MHz): δ=114.41 (d, 1P, $^{2}$J$_{PP}$=116.87 Hz), 104.98 (d, 1P, $^{2}$J$_{PP}$=116.64 Hz).

IR-ATR (solid) $\bar{υ}$ [cm$^{-1}$]: 1894 (s, $\bar{υ}$ CO).

3. Asymmetric Hydrogenation Results

3.1 Hydrogenation of Ketones or Ketoesters with Manganese Complex of Example 2.1

General Procedure:

All catalytic hydrogenation experiments using molecular hydrogen were carried out in a Parr Instruments autoclave (300 mL) advanced with an internal alloy plate include up to 8 uniform reaction vials (4 mL) equipped with a cap and needle penetrating the septum.

Representative Experiment:

Under an argon atmosphere, a vial was charged with Manganese Complex of example 2.1 and base which were dissolved in 2 mL of dried solvent. The resulting red solution was stirred briefly before the ketone or ketoester (0.5 or 1 mmol) was added. The vial was placed in the alloy plate which was then placed into the autoclave. Once sealed, the autoclave was purged 5 times with hydrogen, then pressurized to 30 bar and heated to desired temperature. Afterwards, the autoclave was cooled to RT, depressurized, and the reaction mixture was analyzed by GC-FID or HPLC as well as GC-MS. Product isolation was performed via column chromatography using silica gel as stationary phase and n-pentane/ethylacetate or n-pentane/acetone mixture as eluent.

Individual Reaction Conditions:

[a] 2 mol % cat., 5 mol % NaOtBu, 0.5 mmol substrate, 30 bar, 3 h, 50° C., EtOH (1.5 mL)

[b] 2 mol % cat., 5 mol % NaOtBu, 0.5 mmol substrate, 30 bar, 3 h, 70° C., EtOH (1.5 mL)

[c] 2 mol % cat., 5 mol % NaOtBu, 0.5 mmol substrate, 30 bar, 3 h, 50° C., toluene (1.5 mL)

[d] 2 mol % cat., 5 mol % NaOtBu, 0.5 mmol substrate, 30 bar, 3 h, 50° C., iPrOH (1.5 mL)

[e] 2 mol % cat., 5 mol % NaOtBu, 0.5 mmol substrate, 30 bar, 3 h, 50° C., iPrOH (1.5 mL)

[f] 1 mol % cat., 5 mol % KOtBu, 0.5 mmol substrate, 30 bar, 4-5 h, 40° C., tert-amyl alcohol (1.5 mL)

[g] 1 mol % cat., 5 mol % KOtBu, 0.5 mmol substrate, 30 bar, 16 h, 50° C., toluene (1.5 mL)

[h] 2 mol % cat., 5 mol % KOtBu, 0.5 mmol substrate, 30 bar, 8 h, 100° C., dioxan (1.5 mL)

[i] 1 mol % cat., 5 mol % KOtBu, 1 mmol substrate, 30 bar, 4 h, 30° C., 1,4-dioxane (2 mL)

[j] 1 mol % cat., 5 mol % KOtBu, 1 mmol substrate, 30 bar, 4 h, 40° C., tert-amyl alcohol (2 mL)

[k] 1 mol % cat., 5 mol % KOtBu, 1 mmol substrate, 30 bar, 4 h, 80° C., tert-amyl alcohol (2 mL)

[l] 2 mol % cat., 5 mol % KOtBu, 1 mmol substrate, 30 bar, 4 h, 50° C., toluene (2 mL)

[m] 2 mol % cat., 5 mol % KOtBu, 1 mmol substrate, 30 bar, 4 h, 80° C., tert-amyl alcohol (2 mL)

[n] 2 mol % cat., 5 mol % NaOtBu, 0.5 mmol substrate, 30 bar, 3 h, 70° C., iPrOH (1.5 mL)

[o] 2 mol % cat., 5 mol % NaOtBu, 0.5 mmol substrate, 30 bar, 1 h, 50° C., iPrOH (1 mL)

SP=side product (Hydrogenation of double bond)

TABLE 1

| Example | Substrate | Reaction Conditions | Conversion (%) | e.e. |
|---|---|---|---|---|
| 3.1.1.a | | d | 90 (36 SP) | 67 |
| 3.1.1.b | | o | 90 (36 SP) | 67 (20% for the SP) |
| 3.1.2.a | | f | 65 | 69 |
| 3.1.2.b | | i | 76 | 69 |

TABLE 1-continued

| Example | Substrate | Reaction Conditions | Conversion (%) | e.e. |
|---|---|---|---|---|
| 3.1.3.a | 2-acetylfuran | a | 100 | 68 |
| 3.1.3.b | 2-acetylfuran | i | >99 | 70 |
| 3.1.4.a | 2-acetylbenzofuran | b | 99 | 73 |
| 3.1.4.b | 2-acetylbenzofuran | i | 99 | 74 |
| 3.1.5.a | α-tetralone | a | 30 | 79 |
| 3.1.5.b | α-tetralone | i | 70 | 80 |
| 3.1.6a | 1-indanone | a | 96 | 84 |
| 3.1.6b | 1-indanone | i | 96 | 84 |
| 3.1.7 | benzylideneacetone | a | 87 (13SP) | 59 |
| 3.1.8.a | cyclopropyl methyl ketone | f | 96 | 69 |
| 3.1.8.b | cyclopropyl methyl ketone | j | 96 | 70 |
| 3.1.9.a | cyclopentyl methyl ketone | a | 42 | 52 |
| 3.1.9.b | cyclopentyl methyl ketone | j | 61 | 74 |
| 3.1.9.c | cyclopentyl methyl ketone | k | 96 | 74 |
| 3.1.10.a | cyclohexyl methyl ketone | f | 100 | 86 |
| 3.1.10.b | cyclohexyl methyl ketone | j | >99 | 86 |
| 3.1.11.a | 4-acetyltetrahydropyran | f | 100 | 70 |
| 3.1.11.b | 4-acetyltetrahydropyran | j | 96 | 80 |
| 3.1.12 | 1-acetylcyclohexene | d | 100 (25SP) | 50 |
| 3.1.13.a | 2-cyclohexenone | c | 100 (7 SP) | 64 |

TABLE 1-continued

| Example | Substrate | Reaction Conditions | Conversion (%) | e.e. |
|---|---|---|---|---|
| 3.1.13.b | 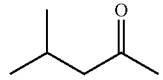 | l | 94 (6 SP) | 62 |
| 3.1.14.a | | f | 44 | 61 |
| 3.1.14.b | | j | 46 | 61 |
| 3.1.15.a | | e | 30 | 51 |
| 3.1.15.b | | n | 30 | 51 |
| 3.1.16 | | j | >99 | 76 |
| 3.1.17 | | j | 26 | 71 |
| 3.1.18 | | j | 23 | 62 |
| 3.1.19 | | j | >99 | 50 |
| 3.1.20 | | m | >99 | 68 |
| 3.1.21 | 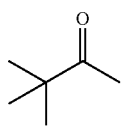 | m | >99 | 31 |
| 3.1.22 | | m | 22 | 29 |
| 3.1.23 | 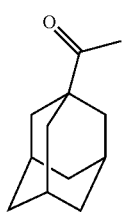 | k | 28 | 99 |

3.2 Hydrogenation of Ketones or Ketoesters with Iron Complex of Example 2.2

General Procedure:

All catalytic hydrogenation experiments using molecular hydrogen were carried out in a Parr Instruments autoclave (300 mL) advanced with an internal alloy plate include up to 8 uniform reaction vials (4 mL) equipped with a cap and needle penetrating the septum.

Representative Experiment:

Under an argon atmosphere, a vial was charged with Iron Complex of example 2.2 which were dissolved in 2 mL of dried solvent. The resulting yellow solution was stirred briefly before the ketone or ketoester (0.5 or 1 mmol). The vial was placed in the alloy plate which was then placed into the autoclave. Once sealed, the autoclave was purged 5 times with hydrogen, then pressurized to 30 bar and heated to desired temperature. Afterwards, the autoclave was cooled to RT, depressurized, and the reaction mixture was analyzed by GC-FID or HPLC as well as GC-MS. Product isolation was performed via column chromatography using silica gel as stationary phase and n-pentane/ethylacetate or n-pentane/acetone mixture as eluent.

Individual Reaction Conditions:

[a] 1 mol % cat., 0.5 mmol substrate, 30 bar, 3 h, 30° C., $CH_2Cl$ (1.5 mL)

[b] 3 mol % cat., 0.5 mmol substrate, 30 bar, 3 h, 70° C., iPrOH (1.5 mL)

[c] 2 mol % cat., 0.5 mmol substrate, 30 bar, 2 h, 50° C., EtOH (1.5 mL)

[d] 1 mol % cat., 0.5 mmol substrate, 30 bar, 3 h, 70° C., iPrOH (1.5 mL)

[f] 1 mol % cat., 1 mmol substrate, 30 bar, 22 h, 40° C., n-heptane (1.5 mL)

[g] 1 mol % cat., 1 mmol substrate, 30 bar, 3 h, 30° C., EtOH (2 mL)

[h] 1 mol % cat., 1 mmol substrate, 30 bar, 6 h, 30° C., EtOH (2 mL)

[i] 1 mol % cat., 1 mmol substrate, 30 bar, 6 h, 60° C., EtOH (2 mL)

[j] 1 mol % cat., 1 mmol substrate, 30 bar, 6 h, 30° C., EtOH (2 mL)

[k] 3 mol % cat., 1 mmol substrate, 30 bar, 3 h, 70° C., THF (2 mL)

SP=side product (Hydrogenation of double bond)

TABLE 2

| Example | Substrate | Reaction Conditions | Conversion (%) | e.e. |
|---|---|---|---|---|
| 3.2.1.a | phenyl cyclohexyl ketone | b | 100 | 35 |
| 3.2.1.b | phenyl cyclohexyl ketone | g | >99 | 35 |
| 3.2.2.a | thiochroman-4-one | c | 96 | 48 |
| 3.2.2.b | thiochroman-4-one | g | >99 | 74 |
| 3.2.3.a | cyclopropyl methyl ketone | c | 100 | 32 |
| 3.2.3.b | cyclopropyl methyl ketone | h | >99 | 34 |
| 3.2.4.a | cyclopentyl methyl ketone | b | 95 | 52 |
| 3.2.4.b | cyclopentyl methyl ketone | h | >99 | 60 |
| 3.2.5.a | cyclohexyl methyl ketone | b | 100 | 64 |
| 3.2.5.b | cyclohexyl methyl ketone | h | >99 | 64 |
| 3.2.6.a | tetrahydropyran-4-yl methyl ketone | c | 100 | 45 |
| 3.2.6 | tetrahydropyran-4-yl methyl ketone | h | >99 | 45 |
| 3.2.7.a | 1-cyclohexenyl methyl ketone | b | 100 (5SP) | 48 |
| 3.2.7.b | 1-cyclohexenyl methyl ketone | k | 97 (3 SP) | 48 |
| 3.2.8.a | 2,2-dimethyl-3-hexanone | d | 98 | 35 |
| 3.2.8.b | 2,2-dimethyl-3-hexanone | i | 36 | 35 |
| 3.2.9.a | pinacolone | d | 100 | 30 |
| 3.2.9.b | pinacolone | h | 17 | 32 |
| 3.2.9.c | pinacolone | i | >99 | 33 |

TABLE 2-continued

| Example | Substrate | Reaction Conditions | Conversion (%) | e.e. |
|---|---|---|---|---|
| 3.2.10.a | isopropyl methyl ketone | d | 100 | 40 |
| 3.2.10.b | isopropyl methyl ketone | h | >99 | 40 |
| 3.2.11.a | methyl acetoacetate | f | 100 | 33 |
| 3.2.11.b | methyl acetoacetate | j | >99 | 33 |
| 3.2.12.a | methyl 2,2-dimethylacetoacetate | b | 100 | 45 |
| 3.2.12.b | methyl 2,2-dimethylacetoacetate | k | >99 | 45 |
| 3.2.13 | 1-indanone | g | >99 | 71 |
| 3.2.14 | α-tetralone | h | 71 | 70 |
| 3.2.15 | benzosuberone | h | 99 | 45 |
| 3.2.16 | chalcone | g | 97 (6 SP) | 56 |
| 3.2.17 | 4-phenyl-2-butanone | h | >99 | 32 |
| 3.2.18 | benzalacetone | h | >99 (2 SP) | 48 |
| 3.2.19 | 2-acetylthiophene | g | >99 | 48 |
| 3.2.20 | 2-acetylbenzofuran | g | >99 | 57 |
| 3.2.21 | cyclohexyl isopropyl ketone | i | 78 | 32 |
| 3.2.22 | 2-cyclohexenone | h | 98 (8 SP) | 46 |
| 3.2.23 | 3-methyl-2-cyclohexenone | h | 99 | 55 |
| 3.2.24 | isophorone | h | 96 | 51 |
| 3.2.25.a | 1-acetyladamantane | h | 61 | >99 |
| 3.2.25.b | 1-acetyladamantane | i | >99 | >99 |

The invention claimed is:

1. A chiral metal complex compound of formula I

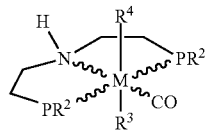

I and its stereoisomers, wherein each ⁓ is independently a broken wedge bond (a) or a solid wedge bond (b)

a) ⋯⋯ b) ━■ ;

M is a metal selected from the manganese group or the iron group of the periodic system;

each $PR^2$ is

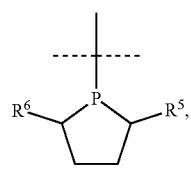

IIa wherein $R^5$ and $R^6$ are each independently $C_{1-4}$-alkyl or aryl; or

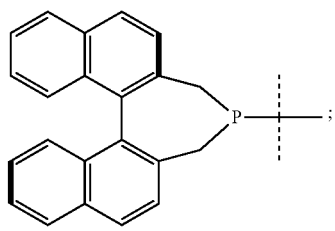

IIb or

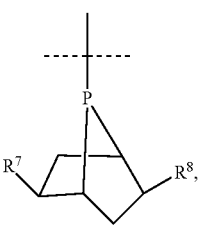

IIc wherein $R^7$ and $R^8$ are each independently $C_{1-4}$-alkyl;

$R^3$ is CO, halogen or hydrogen; and $R^4$ is CO, halogen or H—$BH_3$, wherein the chiral metal complex is in the form of (i) a neutral complex, or (ii) a complex cation with a suitable counter ion.

2. The chiral metal complex compound of claim 1, wherein $R^3$ is CO or hydrogen; and $R^4$ is CO or H—$BH_3$.

3. The chiral metal complex compound of claim 1, wherein M is selected from the manganese group of the periodic system.

4. The chiral metal complex compound of claim 1, wherein M is selected from manganese and iron.

5. The chiral metal complex compound of claim 1, wherein $PR^2$ is

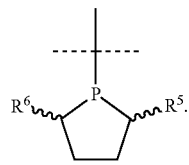

IIa1

6. The chiral metal complex compound of claim 5, wherein $R^5$ and $R^6$ are each independently $C_{1-4}$-alkyl.

7. The chiral metal complex compound of claim 1, wherein $PR^2$ is

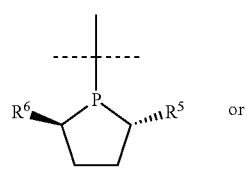

IIa2' or

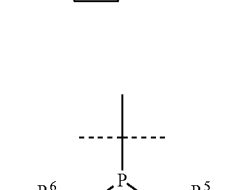

IIa2''

8. The chiral metal complex compound of claim 1, having the structure of formula Ia

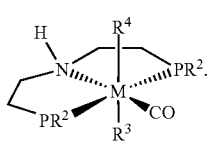

Ia

9. The chiral metal complex compound of claim 1, having the structure of formula Ib

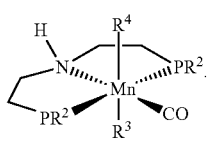

Ib

10. The chiral metal complex compound of claim 1, having the structure of formula Ic

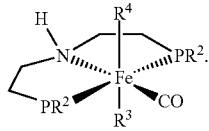
Ic

11. The chiral metal complex compound of claim 1, having the structure of formula Id;

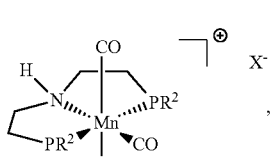
Id wherein
X is a halogen or a pseudohalogen.

12. The chiral metal complex compound of claim 11, wherein X is bromine.

13. The chiral metal complex compound of claim 1, having the structure of formula Ie

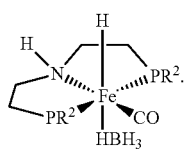
Ie

14. The chiral metal complex compound of claim 1, having the structure of formula If;

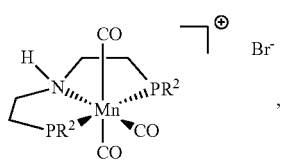
If wherein
PR² is

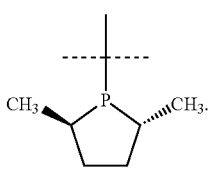

15. The chiral metal complex compound of claim 1, having the structure of formula Ig

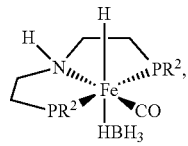
Ig wherein
PR² is

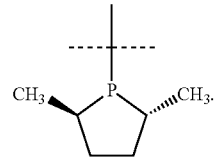

16. A method of catalyzing an asymmetric reaction, said method comprising catalyzing said reaction with a chiral metal complex compound of claim 1.

17. The method of claim 16, wherein the asymmetric reaction is an asymmetric reduction.

18. The method of claim 17, wherein the reduction is an asymmetric reduction of a C=X double bond.

19. The method of claim 18, wherein the C=X double bond is a bond of a ketone, ketoester, imine or oxime.

20. The chiral metal complex compound of claim 1, wherein the metal is selected from the group consisting of manganese, rhenium, iron, ruthenium and osmium.

21. The chiral metal complex compound of claim 1, wherein $R^5$ and $R^6$ are each methyl, or $R^7$ and $R^8$ are each methyl.

22. A process for the preparation of a chiral metal complex compound of formula I, comprising
reacting a Bis(phospholanoethyl)amine derivative of formula III

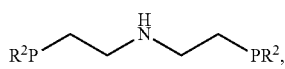
III with $Mn(CO)_5X^-$ to form the chiral metal complex compound of formula Id

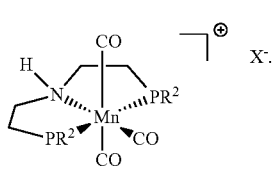
Id with $FeX_2$ to form an iron complex intermediate of the formula IV

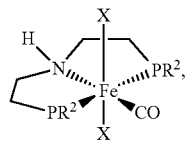

wherein
each PR² is

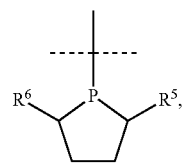

wherein
R⁵ and R⁶ are each independently $C_{1-4}$-alkyl or aryl; or

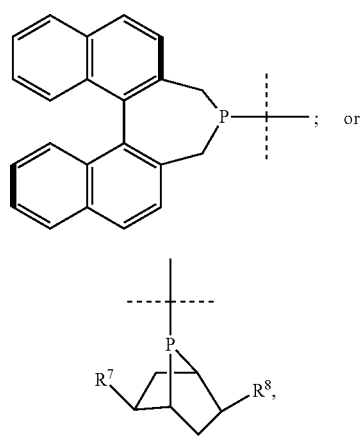

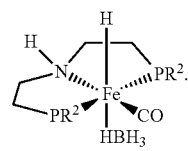

wherein
R⁷ and R⁸ are each independently $C_{1-4}$-alkyl, and wherein X is a halogen or a pseudohalogen.

23. The process of claim 22, wherein:
the iron complex intermediate of formula IV is reacted a hydride-forming agent to form the chiral metal complex compound of formula Ie

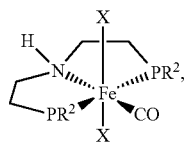

24. A chiral iron complex intermediate of formula IV

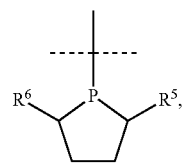

wherein
each PR² is

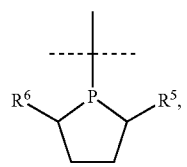

wherein
R⁵ and R⁶ are each independently $C_{1-4}$-alkyl or aryl; or

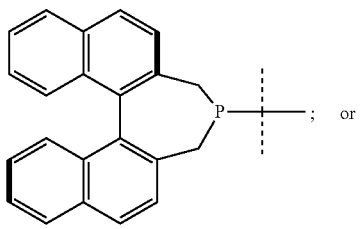

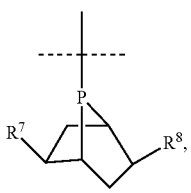

wherein
R⁷ and R⁸ are each independently $C_{1-4}$-alkyl; and
X is a halogen.

25. The chiral iron complex intermediate of claim 24, wherein X is bromine.

* * * * *